United States Patent [19]

Ueno et al.

[11] Patent Number: 5,075,334

[45] Date of Patent: Dec. 24, 1991

[54] EXCRETION OF POTASSIUM ION BY PROSTANOIC ACID DERIVATIVES

[75] Inventors: Ryuji Ueno; Hiroyoshi Osama, both of Hyogo, Japan

[73] Assignee: K.K. Ueno Seiyaku Oyo Kenkyujo, Osaka, Japan

[21] Appl. No.: 557,834

[22] Filed: Jul. 26, 1990

[30] Foreign Application Priority Data

Jul. 27, 1989 [JP] Japan .................................. 1-197090

[51] Int. Cl.⁵ ................... A61K 31/19; A61K 31/215; A61K 31/557
[52] U.S. Cl. ..................................... 514/530; 514/573
[58] Field of Search ................................ 514/573, 530

[56] References Cited

FOREIGN PATENT DOCUMENTS

| | | |
|---|---|---|
| 0281239 | 1/1988 | European Pat. Off. . |
| 0284180 | 1/1988 | European Pat. Off. . |
| 0330511 | 2/1988 | European Pat. Off. . |
| 0289349 | 4/1988 | European Pat. Off. . |
| 0292177 | 5/1988 | European Pat. Off. . |
| 0308135 | 9/1988 | European Pat. Off. . |
| 0310305 | 9/1988 | European Pat. Off. . |
| 0342003 | 5/1989 | European Pat. Off. . |
| 0343904 | 5/1989 | European Pat. Off. . |
| 0345951 | 5/1989 | European Pat. Off. . |

OTHER PUBLICATIONS

Chem. Abst. 90-118674J.
Anggard, Acta Physical. Scand., 1966, 66, pp. 509-510.
Robert et al., Prostaglandins, vol. 11, No. 5, May 1976, pp. 809-828.

*Primary Examiner*—Stanley J. Friedman
*Attorney, Agent, or Firm*—Sughrue, Mion, Zinn, Macpeak & Seas

[57] ABSTRACT

Amethod for inducing decrease in potassium ion concentration in the blood which comprises administering, to a subject having an increased potassium ion concentration in the blood, a prostanoic acid derivative in an amount effective in inducing decrease in potassium ion concentration in the blood wherein said concentration is increased or for improving extracorporeal excretion of potassium ion in the blood which comprises administering, to a subject having an increased potassium ion concentration in the blood, a prostanoic acid derivative in an amount effective in improving extracorporeal excretion of potassium ion concentration is increased.

20 Claims, No Drawings

EXCRETION OF POTASSIUM ION BY PROSTANOIC ACID DERIVATIVES

BACKGROUND OF THE INVENTION

1. Field of the Invention

The present invention relates to a method for improvement of extracorporeal excretion of potassium ion and inducing decrease in potassium ion concentration in the blood which comprises administering a prostanoic acid derivative to a subject.

The object of the present invention is to reduce potassium ion concentration in the blood or improve extracorporeal excretion of potassium ion in the treatment of conditions wherein potassium ion concentration in the blood is increased, e.g. hyperkalemia or renal insufficiency. Generally, potassium ion in the blood is excreted into the urine through the kidneys. According to the present invention, however, potassium ion is excreted through the intestinal wall as an alternative main route, and this route is effective for a patient whose renal function is reduced or injured. This method of excretion may be called "intracorporeal dialysis".

Renal insufficiency refers to a condition in which renal function is injured by renal diseases such as glamerulonephritis, nephrotic syndrome, nephrosclerosis, renal carcinoma, lupus nephritis etc. One important parameter for renal insufficiency is the excreting function of kidney and especially the concentration of potassium ion in the blood which are pooled in the body by injured excretion. Symptom of hyperkalemia appears as the pooling progresses.

Traditional means effective in the treatment of renal insufficiency is the so-called dialysis in which the blood is contacted with a dialysate with a semipermeable membrane between them whereby substances in the blood may be removed through diffusion by osmotic gradient. The dialysis include hemokialysis in which the arterial blood is introduced into an artificial kidney and returned to a vein and peritoneal dialysis in which blood substances are dispersed into a dialysate, which is introduced into the peritoneal cavity and discharged periodically, through capillary vessels serving as a semipermeable membrane. However, the former has disadvantage that it requires a sergical operation such as shunt operation while the latter has disadvantages that it has inferior dialysis efficacy and requires infection-preventing measures.

2. Background Information

The present inventor and co-workers formerly discovered that 15-keto-16-halo-prostaglandins (hereinafter, prostaglandin is referred to as PG) have an enteropooling activity (activity of pooling water in intestines) (EP-A-310305). Enteropooling activity of 16,16-dimethyl-PGE$_2$ has also been described in Prostaglandins, 11, 809–828(1976). However, nothing has been reported about the fact that prostanoic acid derivatives have activity of excreting potassium ion.

As a result of extensive studies about the properties of PG compounds, the present inventors unexpectedly discovered that these compounds have an activity of decreasing potassium ion concentration in the blood and excreting potassium ion.

SUMMARY OF THE INVENTION

In a first aspect, the present invention provides a method for inducing decrease in potassium ion concentration in the blood which comprises administering, to a subject having an increased potassium ion concentration in the blood, a prostanoic acid derivative in an amount effective in inducing decrease in potassium ion concentration in the blood wherein said concentration is increased.

In a second aspect, the present invention provides a method for improving extracorporeal excretion of potassium ion in the blood which comprises administering, to a subject in need of such treatment, an amount, effective in improving extracorporeal excretion of potassium ion in the blood, of a prostanoic acid derivataive.

In a third aspect, the present invention provides a use of a prostanoic acid derivative for the manufacture of a medicament for inducing decrease in potassium ion concentration in the blood.

In a fourth aspect, the present invention provides a use of a prostanoic acid derivative for the manufacture of a medicament for improving extracorporeal excretion of potassium ion in the blood of a patient having an increased potassium ion concentration in the blood.

In a fifth aspect, the present invention provides a pharmaceutical composition for inducing decrease in potassium ion concentration in the blood comprising a prostanoic acid derivative in association with a pharmaceutically acceptable carrier, diluent or excipient.

In a sixth aspect, the present invention provides a pharmaceutical composition for improving extracorporeal excretion of potassium ion in the blood of a patient having an increased potassium ion concentration in the blood comprising a prostanoic acid derivative in association with a pharmaceutically acceptable carrier, diluent or excipient.

DETAILED DESCRIPTION OF THE INVENTION

The expression "extracorporeal excretion" means active or passive transport of substances in the body fluid, principally in the blood, into the urine or feces through the intestine ranging from duodenum to large intestine, principally through small intestine.

The term "prostanoic acid" refers to the basic skeleton, show by the formula below, as the common structural feature of the naturally occurring PGs.

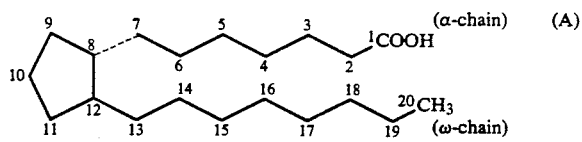

The primary PGs are classified based on the structural feature of the five-membered cycle moiety into PGAs, PGBs, PGCs, PGDs, PGEs, PGFs, PGGs, PGHs, PGIs and PGJs, and also on the presence or absence of unsaturation and oxidation in the chain moiety as:
Subscript 1 - - - 15-OH
Subscript 2 - - - 5,6-unsaturated-15-OH
Subscript 3 - - - 5,6- and 17, 18-diunsaturated-15-OH
Further, PGFs are sub-classified according to the configration of hydroxy group at 9 into α(hydroxy group being in the alpha configration) and β(hydroxy group being in the beta configration). Some synthetic analogues have somewhat modified skeletons.

The term "derivative" refers to a compound in which one or more atom or group in the prostanoic acid shown by the formula (A) is replaced by other atom or group or eliminated. Such derivatization includes the modifications known in the synthetic PG analogues and other modifications.

Nomenclature

Nomenclature of prostanoic acid derivatives herein uses the numbering system of prostanoic acid represented in formula (A) shown above.

While formula (A) shows a basic skeleton having twenty carbon atoms, the 15-keto-PG compounds used in the present invention are not limited to those having the same number of carbon atoms. The carbon atoms in Formula (A) are numbered 2 to 7 on the α-chain starting from the α-carbon atom adjacent to the carboxylic carbon atom which is numbered 1 and towards the five-membered ring, 8 to 12 on the said ring starting from the carbon atom on which the α-chain is attached, and 13 to 20 on the ω-chain starting from the carbon atom adjacent to the ring. When the number of carbon atoms is decreased in the α-chain, the number is deleted in order starting from position 2 and when the number of carbon atoms is increased in the α-chain, compounds are named as substituted derivatives having respective substituents at position 1 in place of carboxy group (C-1). Similarly, when the number of carbon atoms is decreased in the ω-chain, the number is deleted in order starting from position 20 and when the number of carbon atoms is increased in the ω-chain, compounds are named as substituted derivatives having respective substituents at position 20. Stereochemistry of the compounds is the same as that of above formula (A) unless otherwise specified.

In general, PGDs, PGEs and PGFs have (a) hydroxy group(s) on the carbon atom(s) at position 9 and/or 11 but in the present specification PGs include those having a group other than a hydroxyl group at position 9 and/or 11. Such PGs are referred to as 9-dehydroxy-9-substituted-PG compounds or 11-dehydroxy-11-substituted-PG compounds.

As stated above, nomenclature of the prostanoic acid derivative is based upon the prostanoic acid and sometimes utilizes abbreviation "PG" for convenience, when the derivative in question has a partial structural common with PGs. These compounds, however, can also be named according to the IUPAC naming system. For example, 13,14-dihydro-15-keto-16R,S-fluoro-PGE$_2$ is (Z)-7-{(1R,2R,3R)-3-hydroxy-2-[(4R,S)-4-fluoro-3-oxo-1-octyl]-5-oxocyclopentyl}-hept-5-enic acid. 13,14-dihydro-15-keto-20-ethyl-11-dehydroxy-11R-methyl-PGE$_2$ methyl ester is methyl 7-{(1R,2S,3S)-3-methyl-2-[3-oxo-1-decyl]-5-oxo-cyclopentyl}-hept-5-enoate. 13,14-dihydro-6,15-diketo-19-methyl-PGE$_2$ ethyl ester is ethyl 7-{(1R,2S,3S)-3-hydroxy-2-(7-methyl-3-oxo-1-octyl)-5-oxo-cyclopentyl}-6-oxo-heptanoate. 13,14-dihydro-15-keto-20-ethyl-PGF$_{2\alpha}$ isopropyl ester is isopropyl (Z)-7-[(1R,2R,3R,5S)-3,5-dihydroxy-2-{3-oxo-1-decyl)-cyclopentyl]-hept-5-enoate. 13,14-dihydro-15-keto-20-methyl-PGF$_{2\alpha}$ methyl ester is methyl (Z)-7-[(1R,2R,3R,5S)-3,5-dihydroxy-2-{3-oxo-1-nonyl}-cyclopentyl]-hept-5-enoate.

Preferred Compounds

Preferred prostanoic acid derivatives used in the present are those having an oxo group at position 15 of the prostanoic acid in place of the hydroxy group, or having at least one halogen atom on the prostanoic acid skeleton, or having both of these features. These derivatives may have a single bond (15-keto-PG$_1$ compounds), a double bond (15-keto-PG$_2$ compounds) between positions 5 and 6, or two double bonds (15-keto-PG$_3$ compounds) between positions 5 and 6 as well as positions 17 and 18.

The term "halogen" refers to fluorine, chlorine, bromine and iodine with fluorine being preferred.

Examples of substitution products or derivatives include esters at the carboxy group at the alpha chain, pharmaceutically or physiologically acceptable salts, unsaturated derivatives having a double bond or a triple bond between positions 2 and 3 or positions 5 and 6, respectively, substituted derivatives having substituent(s) on carbon atom(s) at position 3, 6, 16, 17, 19 and/or 20 and compounds having lower alkyl or a hydroxy (lower) alkyl group at position 9 and/or 11 in place of the hydroxy group, of the above PGs.

Examples of substituents present in preferred compounds are as follows: Substituents on the carbon atom at position 3, 17 and/or 19 include lower alkyl, for example, $C_{1-4}$ alkyl, especially methyl and ethyl. Substituents on the carbon atom at position 16 include lower alkyl e.g. methyl, ethyl etc., hydroxy and halogen atom e.g. chlorine, fluorine, phenyl and phenoxy, the last two being unsubstituted or substituted. Substituents on the carbon atom at position 20 include saturated and unsaturated lower alkyl e.g. $C_{1-4}$ alkyl, lower alkoxy e.g. $C_{1-4}$ alkoxy and lower alkoxy (lower) alkyl e.g $C_{1-4}$ alkoxy-$C_{1-4}$ alkyl Substituents on the carbon atom at position 6 include oxo group forming carboxyl. Stereochemistry of PGs having hydroxy, lower alkyl or lower (hydroxy) alkyl substituent on the carbon atom at position 9 and/or 11 may be alpha, beta or mixtures thereof.

Said derivatives may have an alkoxy, phenoxy or phenyl group at the end of the omega chain where the chain is shorter than the primary PGs.

In the present invention, preferred compounds are those having at least one halogen atom on the prostanoic acid derivative, and the position of halogen atom is not limited but preferredly on the omega chain and more preferredly one or two halogen atoms are present at position 16.

A group of preferred compounds used in the present invention has the formula (I)

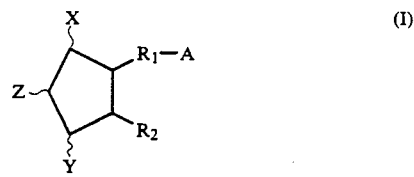

wherein X and Y are hydrogen, hydroxy, halo, lower alkyl, hydroxy(lower)alkyl, or oxo, with the proviso that at least one of X and Y is a group other than hydrogen, and 5-members ring may have at least one double bond, Z is hydrogen or halogen, A is —CH$_2$OH, —COCH$_2$OH, —COOH or its functional derivative, R$_1$ is bivalent saturated or unsaturated, lower or medium aliphatic hydrocarbon residue which is unsubstituted or substituted with halo, oxo or aryl, R$_2$ is saturated or unsaturated, lower or mediumaliphatic hydrocarbon residue which is unsubstituted or substituted with oxo, hydroxy, halo, lower alkoxy, lower alkanoyloxy, cyclo(lower)alkyl, aryl or aryloxy, with the proviso the third carbon atom counted from 5-membered ring is substituted with an oxo group.

In the above formula, the term "unsaturated" in the definitions for R$_1$ and R$_2$ is intended to include at least one and optionally more then one double bond and/or triple bond isolatedly, separately or serially present between carbon atoms of the main and/or side chains. According to usual nomenclature, an unsaturation between two serial positions is represented by denoting the lower number of said two positions, and an unsaturation between two distal positions is represented by denoting both of the positions. Preferred unsaturation is a double bond at position 2 and a double or triple bond at position 5.

The term "lower or medium aliphatic hydrocarbon residue" refers to a straight or branched chain hydrocarbyl group having 1 to 14 carbon atoms (for a side chain, 1 to 3 carbon atoms being preferred) and preferably 2 to 8 carbon atoms for $R_1$ and 6 to 12 carbon atoms for $R_2$.

The term "halo" denotes fluoro, chloro, bromo and iodo.

The term "lower" is intended to include a group having 1 to 6 carbon atoms unless otherwise specified.

The term "lower alkyl" as a group or a moiety in hydroxy(lower)alkyl includes saturated and straight or branched chain hydrocarbon radicals containing 1 to 6, carbon atoms, e.g. methyl, ethyl, propyl, isopropyl, butyl, isobutyl, t-butyl, pentyl and hexyl.

The term "lower alkoxy" refers to the group lower-alkyl-O- wherein lower alkyl is as defined above.

The term "hydroxy(lower)alkyl" refers to alkyl as defined above and substituted with at least one hydroxy group, e.g. hydroxymethyl, 1-hydroxyethyl, 2-hydroxyethyl and 1-methyl-1-hydroxyethyl.

The term "lower alkanoyloxy" refers to a group of the formula: RCO—O— wherein RCO— is an acyl group formed by oxidation of a lower alkyl group as defined above, e.g. acetyl.

The term "cyclo(lower)alkyl" refers to a cyclic group formed by cyclization of a lower alkyl group as defined above.

The term "aryl" includes unsubstituted or substituted aromatic carbocyclic or heterocyclic (preferably monocyclic) groups, e.g. phenyl, tolyl, xylyl and thienyl. Examples of substituents are halo and halo(lower)alkyl wherein halo and lower alkyl being as defined above.

The term "aryloxy" refers to a group of the formula: ArO— wherein Ar is aryl as defined above.

The term "functional derivative" of carboxy as A includes salts (preferably pharmaceutically acceptable salts), esters and amides.

Suitable "pharmaceutically acceptable salts" includes conventional non-toxic salts, and may be a salt with an inorganic base, for example a metal salt such as an alkali metal salt (e.g. sodium salt, potassium salt, etc.) and an alkaline earth metal salt (e.g. calcium salt, magnesium salt, etc.), ammonium salt, a salt with an organic base, for example, an amine salt (e.g. methylamine salt, dimethylamine salt, cyclohexylamine salt, benzylamine salt, piperidine salt, ethylenediamine salt, ethanolamine salt, diethanolamine salt, triethanolamine salt, tris(hydroxymethylamino)methane salt, monomethyl-monoethanolamine salt, procaine salt, caffeine salt, etc.), a basic amino acid salt (e.g. arginine salt, lysine salt, etc.), tetraalkylammonium salt and the like. These salts can be prepared by the conventional process, for example from the corresponding acid and base or by salt interchange.

Examples of the esters are aliphatic esters, for example, lower alkyl ester e.g. methyl ester, ethyl ester, propyl ester, isopropyl ester, butyl ester, isobutyl ester, t-butyl ester, pentyl ester, 1-cyclopropylethyl ester, etc., lower alkenyl ester e.g. vinyl ester, allyl ester, etc., lower alkynyl ester e.g. ethynyl ester, propynyl ester, etc., hydroxy(lower) alkyl ester e.g. hydroxyethyl ester, lower alkoxy(lower)-alkyl ester e.g. methoxymethyl ester, 1-methoxyetyl ester, etc., and aromatic esters, for example, optionally substituted aryl ester e.g. phenyl ester, tosyl ester, t-butylphenyl ester, salicyl ester, 3,4-di-methoxy-phenyl ester, benzamidophenyl ester etc., aryl(lower)alkyl ester e.g. benzyl ester, trityl ester, benzhydryl ester, etc. Examples of the amides are mono- or di- lower alkyl amides e.g. methylamide, ethylamide, dimethylamide, etc., arylamide e.g. anilide, toluidide, and lower alkyl- or aryl-sulfonylamide e.g. methylsulfonylamide, ethylsulfonylamide, tolylsulfonylamide etc.

Preferred examples of A include —COOH, —COOCH$_3$, —COOCH$_2$ CH$_3$, —COOCH(CH$_3$)$_2$ and —CONHSO$_2$CH$_3$.

The configration of the ring and the α- and/or omega chain in the above formula (I) may be the same as or different from that in the primary PGs. However, the present invention also includes a mixture of a compound having a primary configuration and that of an unprimary configuration.

Examples of the typical compounds of the present invention are 15-keto-PGs, 13,14-dihydro-15-keto-PGs and their e.g. 6-keto-derivatives, $\Delta^2$-derivatives, 3R,S-methyl-derivatives, 16R,S-methylderivatives, 16,16-dimethyl-derivatives, 16R,S-fluoroderivatives, 16,16-difluoro-derivatives, 17S-methylderivatives, 19-methyl-derivatives, 20-methyl-derivatives and 16-desbutyl-16-phenoxy derivatives.

When 15-keto-PG compounds of the present invention have a saturated bond between positions 13 and 14, these compounds may be in the keto-hermiacetal equilibrium by forming a hemiacetal between hydroxy group at position 11 and ketone at position 15.

The proportion of both tautomeric isomers, when present, varies depending on the structure of the rest of the molecule or kind of any substituent present and, sometimes, one isomer may predominantly be present in comparision with the other. However, in this invention, it is to be appreciated that the compounds used in the invention include both isomers. Further, while the compounds used in the invention may be represented by a structure or name based on keto-form regardless of the presence or absence of the isomers, it is to be noted that such structure or name does not intend elimination of the hemiacetal type of compounds.

In the present invention, any of the individual tautomeric isomers, a mixture thereof, or optical isomers, a mixture thereof, a racemic mixture, and other isomers such as steric isomers can be used in the same purpose.

Some of the compounds used in the present invention may be prepared by the method disclosed in Japanese Patent Publication (unexamined) No. A-52753/1989.

Alternatively, these compounds may be prepared by a process analogous to that described herein or to known processes.

A practical preparation of the prostanoic acid derivative, e.g. 13,14-dihydro-15-keto compounds, involves the following steps; referring to the synthetic charts(I) to (III), reaction of the aldehyde (2) prepared by the Collins oxidation of commercially available (—)-Corey lactone (1) with dimethyl (2-oxoheptyl)phosphate anion to give α,β-unsaturated ketone (3), reduction of the α,β-unsaturated ketone (3) to the corresponding saturated ketone (4), protection of the carbonyl group of the ketone (4) with a diol to the corresponding ketal (5), and deprotection of the p-phenylbenzoyl group to give the corresponding alcohol (6) followed by protection of the newly derived hydroxy group with dihydropyrane to give the corresponding tetrahydropyranyl ether (7). According to the above process, a precursor of PGEs wherein the ω-chain is a 13,14-dihydro-15-keto-alkyl group is prepared.

Using the above tetrahydropyranyl ether (7), 6-keto-PGE$_1$s (15) of which a group constituted with carbon atoms of position 5, 6 and 7 is —C$_5$H$_2$—C$_6$(O)—C$_7$H$_2$—, may be prepared in the following steps; reduction of the tetrahydropyranyl ether (7) with, for example, diisobutyl aluminum hydride to give the corresponding lactol (8), reaction of the lactol (8), with the ylide generated from (4-carboxybutyl)triphenyl phosphonium bromide followed by esterification (10), cyclization between the 5,6-double bond and the hydroxyl group at position 9 with NBS or iodine to give the halogenated compound (11), dehydrohalogenation of the compound (11) with, for example, DBU to give the 6-keto compound (13) followed by Jones oxidation and removal of the protecting groups.

Furthermore, PGE$_2$s (19) of which a group constituted with carbon atoms of position 5, 6 and 7 is —C$_7$H$_2$—C$_6$H=C$_5$H— may be prepared in the following steps; as shown in the synthetic chart II, reduction of the above tetrahydropyranyl ether (7) to give the lactol (8), reaction of the resultant lactol (8) with the ylide derived from (4—carboxybutyl-)triphenyl phosphonium bromide to give the carboxylic acid (16) followed by esterification to give ester (17), Jones oxidation of the esters (17) to give the compound (18), and removal of the protecting groups.

Using the above tetrahydropyranyl ether (7) as the starting material, the compound having —C$_7$H$_2$—C$_6$H$_2$—C$_5$H$_2$— may be prepared by using the same process as that for preparing PGE$_2$ having —CH$_2$CH=CH— and subjecting the resultant compound (18) to catalytic reduction to reduce the double bond between the position 5 and 6 followed by removal of the protective groups.

Synthesis of 5,6-dehydro-PGE$_2$s having —C$_7$H$_2$—C$_6$≡C$_5$— may be carried out by capturing a copper enolate formed by 1,4-addition of a monoalkylcopper complex or a dialkylcopper complex of the following formulae:

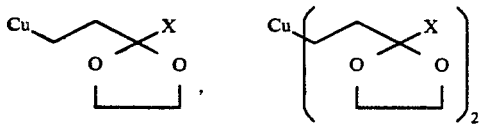

to 4R-t-butyldimethylsilyloxy-2-cyclopenten-1-one with 6-alkoxycarbonyl-1-iodo-2-hexyne or the derivatives.

The 11-β type PGEs can be prepared according to the synthetic chart III.

PGE derivatives having a methyl group at position 11 in place of hydroxy can be prepared by reacting a dimethyl copper complex with PGA-type compound obtained by subjecting 9-hydroxy-11-tosylate to the Jones oxidation. Alternatively, they can be prepared by protecting the carbonyl of saturated ketone (4) produced by reducing unsaturated ketone (3), eliminating p-phenylbenzoyl and tosylating the produced alcohol, treating with DBU to form a lactol, introducing the alpha-chain by Wittig reaction, oxidizing the alcohol at position 9 to give PGA-type compound, and reacting the product with dimethyl copper complex in order to introduce a methyl group into position 11 to give an 11-methyl-PGE-type compound, which on reduction with e.g. sodium borohydride gives an 11-methyl-PGF-type compound. An 11-hydroxymethyl-PGE-type compound, is obtained by a benzophenone-sensitized photoaddition of methanol of PGA-type compound, which is reduced with, e.g. sodium borohydride, to give an 11-hydroxymethyl-PGF-type compound. The synthetic route for the compounds used in the present invention is not limited to the that described above one and may vary using different protecting, reducing and/or oxidizating methods.

Corresponding other PG compounds can be produced analogously.

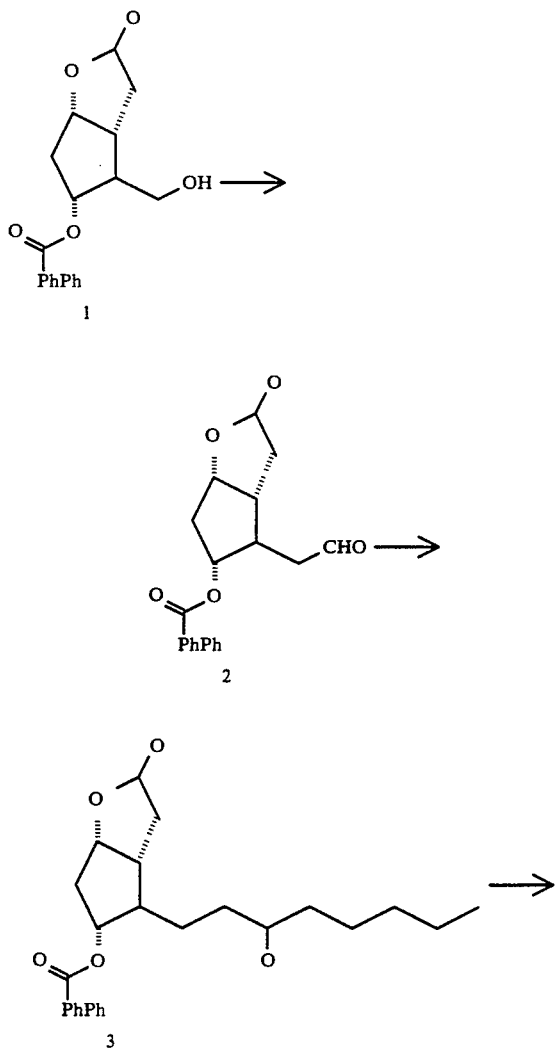

Synthetic Chart I 5,075,334
-continued
Synthetic Chart I
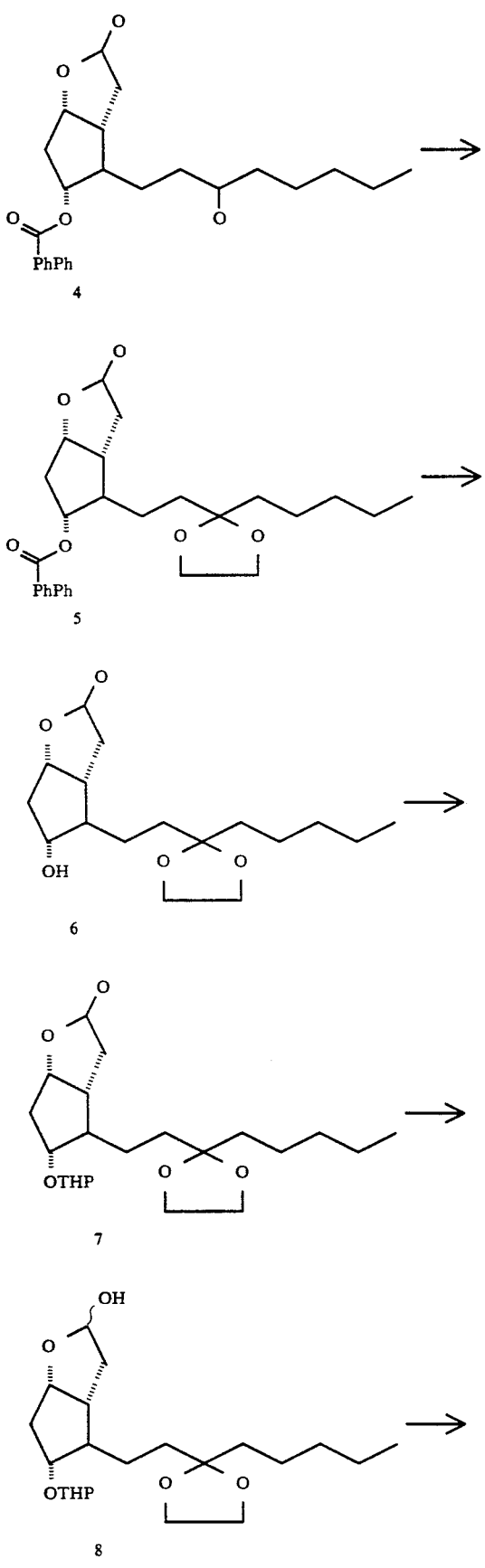
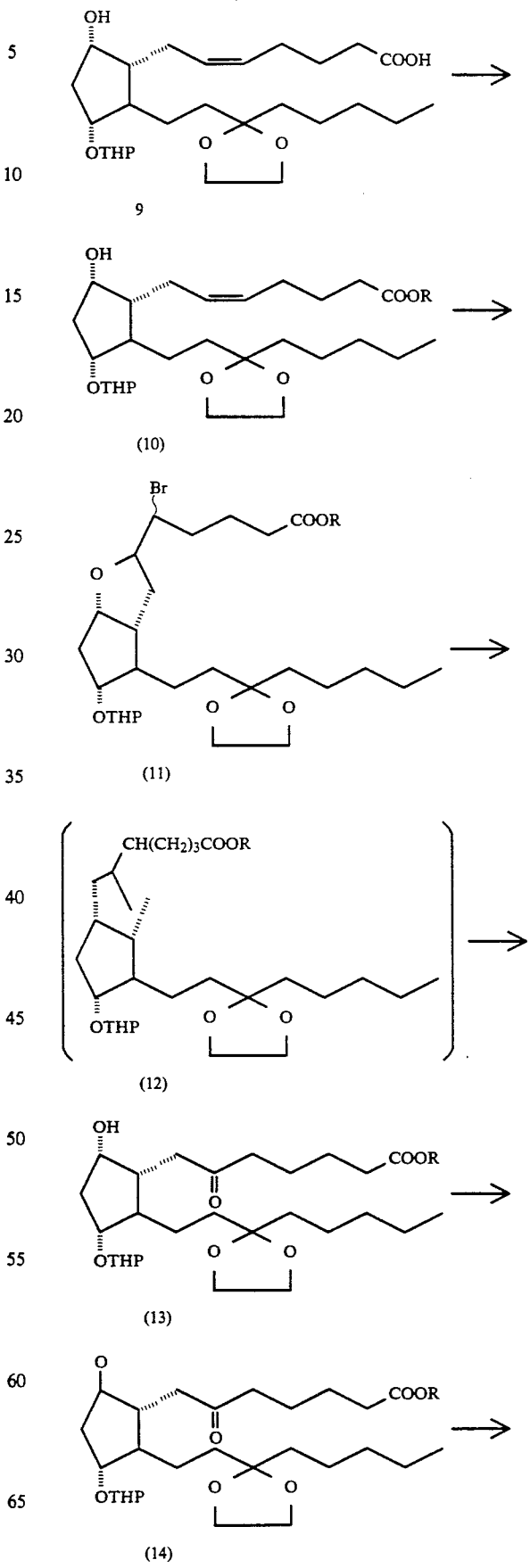

5,075,334
-continued
Synthetic Chart I
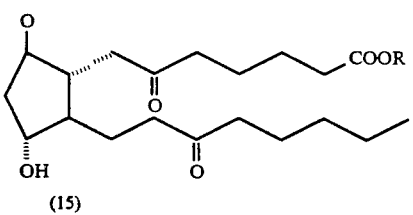
(15)
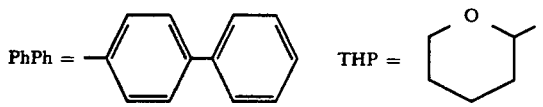
Synthetic Chart II
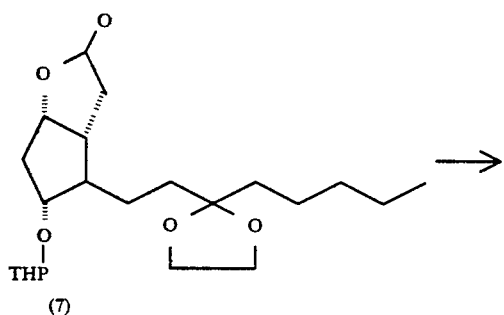
(7)
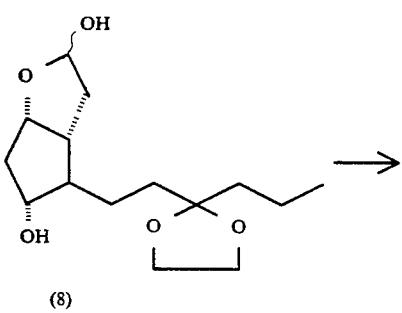
(8)
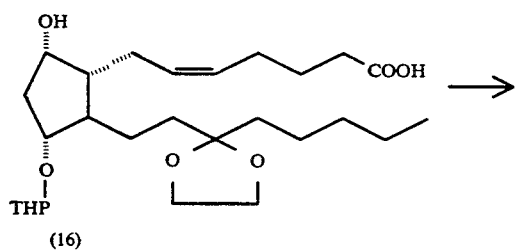
(16)
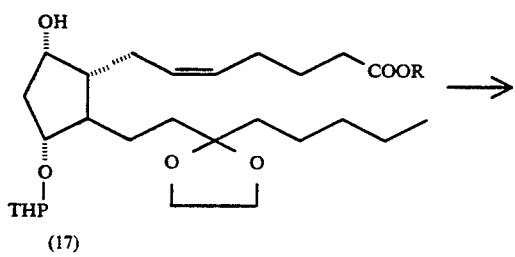
(17)
-continued
Synthetic Chart II
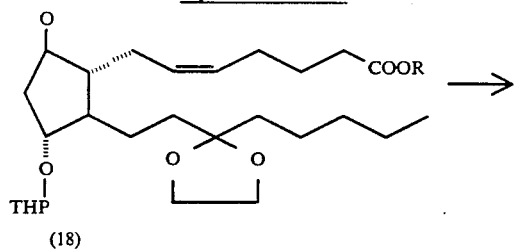
(18)
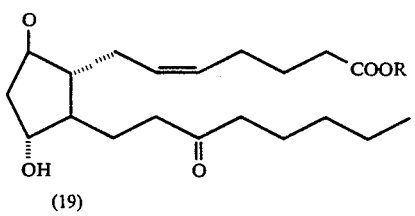
(19)
Synthetic Chart III
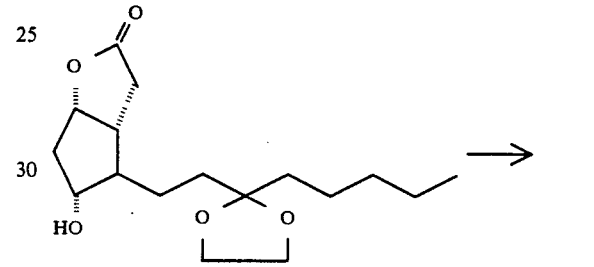
6
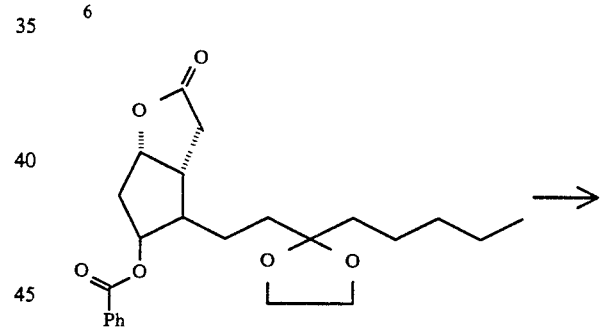
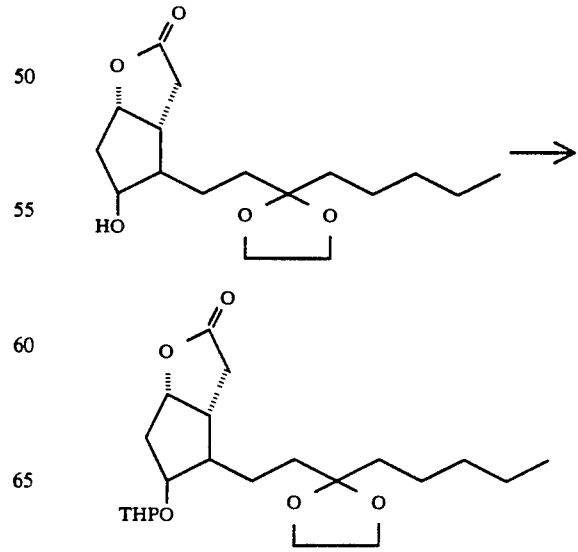

-continued
Synthetic Chart III

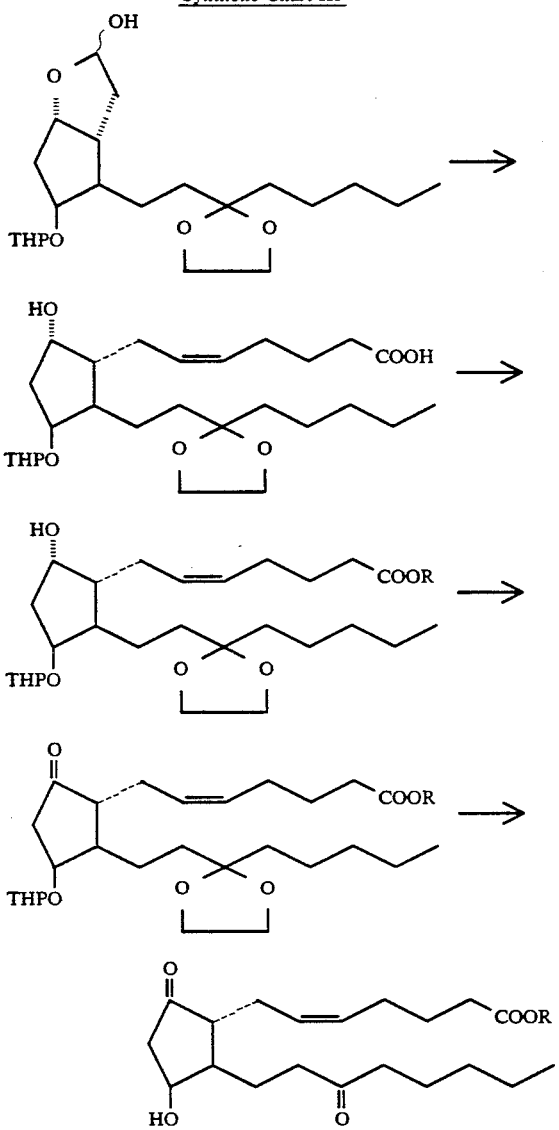

The compounds used in the present invention may be used as a medicine for animals and human beings and usually applied systemically or locally by such methods as oral administration, intravenous injection (including instillation), subcutaneous injection, suppository and the like. While the dosage will vary depending on the particular animal or human patient, age, body weight, symptom to be treated, desired therapeutic effect, administration route, term of treatment and the like, satisfactory effects will be obtained with the dosage of 0.001-500 mg/kg administered in 2 to 4 divided doses a day or as a sustained form.

As a solid composition of this invention for oral administration, tablets, troches, buccals, capsules, pills, powders, granules and the like are included. The solid composition containing one or more active substances is mixed with at least an inactive diluent, e.g. lactose, mannitol, glucose, hydrocypropyl cellulose, fine crystalline cellulose, starch, polyvinyl pyrolidone, magnesium aluminate metasilicate. The composition may contain additives other than the inactive diluent, for example, lubricants e.g., magnesium stearae, a disintegrator e.g. cellulose calcium gluconates, stabilizers e.g. $\alpha$-, $\beta$- or $\gamma$-cyclodextrins, etherated cyclodextrins (e.g. di- methyl-$\alpha$-, dimethyl-$\beta$-, trimethyl-$\beta$-, or hydroxypropyl-$\beta$-cyclodextrins), branched cyclodextins (e.g. glucosyl- or maltosyl-cyclodextrins), formyl cyclodextrins, sulfur-containing cyclodextrins, misoprotols or phospholipids. Such cyclodextrins may increase the stability of the compounds by forming an inclusion compounds. The stability may be often increased by forming lyposome with phospholipids. Tablets and pills may be coated with an enteric or gastroenteric film e.g. white sugar, gelatin, hydroxypropylcellulose, hydroxypropylmethylcellulose phthalates and the like, if necessary, and furthermore they may be covered with two or more layers. Additionally, the composition may be in the form of capsules made of substance easily absorbed e.g. gelatin. The composition may be in the form of buccals, when an immediated effect is desired. For this purpose, base e.g. glycerine, lactose may be used.

Liquid compositions for oral administration include pharmaceutically acceptable emulsions, solutions, suspensions, syrups, elixirs and the like and contain a generally used inactive diluent e.g. purified water or ethyl alcohol. The composition may contain additives e.g. wetting agents, suspending agents, sweeteners, flavors, perfumes and preservatives.

The composition of the present invention may be sprays which may contain one or more active ingredients and which can be prepared according to a well known methods.

An injection of this invention for non-oral administration includes serile aqueous or nonaqueous solutions, suspensions, and emulsions. Diluents for the aqueous solution or suspension include, for example, distilled water for injection, physiological saline and Ringer's solution. Diluents for the nonaqueous solution and suspension include, for example, propylene glycol, polyethylene glycol, vegetable oils e.g. olive oil, alcohols, e.g. ethanol and polysorbates. The composition may contain other additives, e.g. preservatives, wetting agents, emulsifying agents, dispersing agents and the like. These are sterilized by filtration through, e.g. a bacteria- retaining filter, compounding with a sterilizer, gas sterilization or radiation sterilization. These can be prepared by producing a sterilized water or a sterilized solvent for injection before use.

Another formulation according to the present invention is a rectal or vaginal suppository. This can be prepared by mixing at least one active compound according to the invention with a suppository base e.g. cacao butter and optionally containing nonionic surfactant for improving absorption.

The compounds used in the medicament according to the present invention have an effect of inducing decrease in potassium ion concentration or of improving excretion of potassium ion concentration in the blood into the intestines or as feces.

Accordingly, the compounds used in the present invention are useful for treatment (e.g. prevention, cure, relief and arrest or relief of development) of conditions wherein potassium ion level in the blood is elevated and of disorder in the balance of electrolytes such as uremia, irrespective of cause, e.g. disease, drug or food.

A more complete understanding of the present invention can be obtained by reference to the following Formulation Examples and Test Examples which are provided herein for purpose of illustration only and are not intended to limit the scope of the invention.

Formulation Example 1

(Hard Gelatin Capsules)

13,14-dihydro-15-keto-16R,S-fluoro-PGE$_2$: 50 mg
lactose: 200 mg

The above ingredients were mixed and filled in hard gelatin capsules.

Formulation Example 2

| (Powders for injection) | (Parts by weight) |
| --- | --- |
| 13,14-dihydro-15-keto-16,16-difluoro-PGE$_2$ | 1 |
| mannitol | 5 |
| distilled water | 0.4 |

The above ingredients were mixed, stirred, sterilized, filtered and lyophilized to give powders for injection.

Formulation Example 3

| (Injectable solution) | (Parts by weight) |
| --- | --- |
| 13,14-dihydro-15-keto-16,16-dimethyl-PGE$_2$ | 0.2 |
| nonion surfactant | 2 |
| distilled water | 98 |

The above ingredients were mixed and sterilized to give and injectable solution.

Formulation Example 4

13,14-dihydro-15-keto-16,16-difluoro-20-ethyl-PGE$_2$ (50 mg) dissolved in methanol (10 ml) was mixed with mannitol (18.5 g). The mixture was screened (with a sieve, the pore size of which being 30 mm in diameter), dried and screened again. The powders thus obtained were mixed with fine-grain silica gel (Aerosil*, 200 g) and filled in No.3 hard gelatin capsules (100) to give enteric capsules which contain 0.5 mg of 13,14-dihydro-15-keto-16,16-difluoro-20-ethyl-PGE$_2$ per capsule.
* Trade Mark

Formulation Example 5

| (Powders for oral administration) | (Parts by weight) |
| --- | --- |
| 13,14-dihydro-15-keto-16,16-difluoro-PGF$_{2\alpha}$ methyl ester | 5 |
| light anhydrous silicic acid | 5 |
| Abicel* | 20 |
| lactose | 70 |

*Trade Mark

The above ingredients were mixed to give powders for oral administration.

Formulation Example 6

| (Soft gelatine capsules) | (Parts by weight) |
| --- | --- |
| 13,14-dihydro-15-keto-20-methyl-PGE$_2$ methyl ester | 1 |
| light anhydrous silicic acid | 899 |
| Panasate* | 20 |

*Trade Mark

The above ingredients were mixed and filled in soft gelatine capsules.

Formulation Example 7

(Enteric capsules)

16-desbutyl-13,14-dihydro-15-keto-16-(m-trifluoromethyl)phenoxy-PGF$_{2\alpha}$ methyl ester (50 mg) dissolved in methanol (10 ml) was mixed with mannitol (18.5 g). The mixture was screened (with a sieve, the pore size of which being 30 mm in diameter), dried for 90 minutes at 30° C. and screened again. The powders thus obtained were mixed with fine-grain silica gel (Aerosil*, 200 g) and filled in No.3 hard gelatin capsules (100) to give enteric capsules which contain 0.5 mg of 13,14-dihydro-15-keto-16-desbutyl-16-m-trifluoromethylphenoxy-PGF$_{2\alpha}$ methyl ester per capsule.
* Trade Mark In the above formulation examples, the active ingredient can be replaced by any other compound within the compounds used in the invention.

Test Example 1

Thirty male Crj: Wistar rats (5 weeks old, obtained from Charles River) were quarantined and acclimatized for about 1 weeks. Then the animals were divided into groups with even mean weight and standard deviation.

All the animals were bred in individual stainless steel cages (190×380×180 mm) at a temperature of 24°±1° C. and with a humidity of 55±5% with 12 hour light and dark cycle (illumination 8:00–20:00) supplying with fresh aseptic air. They were bred (with NMF, Oriental Yeast Industries, Ltd) and waterad ad libitum exept the last day of medication, on which day they were fasted.

Test compound 13,14-dihydro-15-keto-16-R,S-fluoroprostaglandin E$_2$ was dissolved in an aliquot of ethanol and the solution was evaporated in a test tube under nitrogen. The residue was combined with a predetermined amount of distilled water and sonicated to form a homogeneous test suspension.

Starting from day 1 to day 14, rats received (between 9:00 and 12:00) a daily dosage of 1 ml/1 kg of the test suspension through a disposable plastic sylinge (1 ml) equipped with an P.O. administration needle for rat based on the body weight measured just before the administration.

Design of the experiment was as follows:

| Group | Dose (mg/kg) | Number of rats |
| --- | --- | --- |
| 1 | 0 | 5 |
| 2 | 0.1 | 5 |
| 3 | 2.0 | 5 |

All the animals were observed twice a day for any mortality and general conditions such as diarrhea except the last day, on which observation was made only once directly before the post mortem. The body weight and intake were measured every day at the predetermined time (between 9:00–10:00) before the medication. Urine collection (24 hr) was made 3 hours after the medication under fasting on day 13.

Directly after the last medication, rats were sacrificed by cervical dislocation and subjected to celiotomy. Intestine was ligated at pyloric part of stomach and upper cecal part. The whole small intestine was removed and intraintestinal content was collected, measured a volume and centrifuged for 5 minutes at 1000 rpm and suppernatant was separated.

The urine, serum and supernatant were assayed for electolyte concentrations.

The results are summarized in the following Tables.

samples were taken from tail vein of each animal and serum was assayed for Na, K and Cl concentrations.

In addition two weeks after the start of medication,

TABLE 1

Body weight

| Dosage | Day | Weight (g) | | | | | | | | | | | | | |
|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 |
| 0 (Control) | n | 5 | 5 | 5 | 5 | 5 | 5 | 5 | 5 | 5 | 5 | 5 | 5 | 5 | 5 |
| | mean | 277.7 | 282.0 | 291.9 | 296.2 | 307.3 | 312.3 | 320.4 | 329.7 | 334.9 | 340.8 | 346.4 | 350.1 | 356.0 | 318.0 |
| | S.D. | 4.1 | 7.9 | 6.7 | 7.6 | 10.8 | 10.9 | 12.5 | 10.8 | 11.7 | 14.1 | 15.6 | 15.2 | 16.5 | 13.5 |
| 0.1 mg/kg | n | 5 | 5 | 5 | 5 | 5 | 5 | 5 | 5 | 5 | 5 | 5 | 5 | 5 | 5 |
| | mean | 277.6 | 281.8 | 293.4 | 297.1 | 300.3 | 310.8 | 320.8 | 330.4 | 335.8 | 339.4 | 344.5 | 351.3 | 355.9 | 317.0 |
| | S.D. | 4.1 | 4.9 | 7.4 | 6.0 | 13.0 | 7.1 | 6.7 | 8.4 | 8.3 | 6.6 | 12.4 | 8.8 | 11.1 | 10.9 |
| 2.0 mg/kg | n | 5 | 5 | 5 | 5 | 5 | 5 | 5 | 5 | 5 | 5 | 5 | 5 | 5 | 5 |
| | mean | 277.6 | 274.7 | 283.0 | 286.7 | 296.9 | 300.7 | 309.6 | 319.9 | 322.7 | 327.8 | 330.8 | 334.1 | 345.9 | 304.9 |
| | S.D. | 3.0 | 5.0 | 3.7 | 4.5 | 4.8 | 4.8 | 4.6 | 8.2 | 6.5 | 8.7 | 6.8 | 7.7 | 7.9 | 6.6 |

TABLE 2

Intake

| Dosage | Day | Intake (g) | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| 0 (Control) | n | 5 | 5 | 5 | 5 | 5 | 5 | 5 | 5 | 5 | 5 | 5 | 5 |
| | mean | 27.8 | 28.5 | 29.8 | 28.2 | 28.2 | 30.0 | 29.1 | 29.1 | 30.1 | 29.3 | 29.9 | 29.7 |
| | S.D. | 3.1 | 2.6 | 2.6 | 1.9 | 3.0 | 2.1 | 2.4 | 2.4 | 2.7 | 3.1 | 2.1 | 2.9 |
| 0.1 mg/kg | n | 5 | 5 | 5 | 5 | 5 | 5 | 5 | 5 | 5 | 5 | 5 | 5 |
| | mean | 25.9 | 28.6 | 29.1 | 24.4 | 29.3 | 30.7 | 29.5 | 29.3 | 28.8 | 29.4 | 29.1 | 28.6 |
| | S.D. | 2.9 | 1.3 | 1.4 | 6.6 | 2.5 | 1.5 | 2.5 | 0.1 | 0.9 | 3.4 | 1.0 | 1.7 |
| 2.0 mg/kg | n | 5 | 5 | 5 | 5 | 5 | 5 | 5 | 5 | 5 | 5 | 5 | 5 |
| | mean | *19.3 | 24.8 | 26.1 | 25.2 | 26.3 | 28.1 | 29.0 | 27.8 | 28.7 | 29.1 | 28.0 | 30.9 |
| | S.D. | 1.4 | 1.6 | 2.6 | 2.3 | 2.3 | 2.3 | 2.7 | 1.0 | 1.0 | 2.7 | 2.7 | 2.5 |

*$0.05 > P > 0.01$
(DUNNET ANALYSIS)

TABLE 3

Electrolyte
(I.C.: Intraintestinal content)

| Dosage | | Urine I.C. ml | Urine (3 hr) ml | Na+ I.C. mEq | Na+ Urine mEq | K+ I.C. mEq | K+ Urine mEq | Cl− I.C. mEq | Cl− Urine mEq |
|---|---|---|---|---|---|---|---|---|---|
| 0 (Control) | mean | 2.2 | 3.9 | 0.38 | 0.17 | 0.022 | 0.30 | 0.148 | 0.175 |
| | S.D. | 1.2 | 2.1 | 0.17 | 0.09 | 0.010 | 0.16 | 0.082 | 0.121 |
| 0.1 mg/kg | mean | 2.0 | 1.6 | 0.27 | 0.07 | *0.045 | 0.20 | 0.172 | 0.125 |
| | S.D. | 0.4 | 0.8 | 0.06 | 0.06 | 0.017 | 0.12 | 0.045 | 0.126 |
| 2.0 mg/kg | mean | *4.8 | 1.8 | 0.64 | 0.09 | **0.096 | 0.12 | **0.527 | 0.059 |
| | S.D. | 1.8 | 1.0 | 0.25 | 0.06 | 0.027 | 0.05 | 0.217 | 0.033 |

**$0.1 > P$
*$0.05 > P > 0.01$
(DUNNET analysis)

From the above results, it can be easily understood that excretion of potassium ion into the intestine was dose-dependently increased in the medicated group. Almost no influence was observed in the medicated group in respect to body weight and water intake.

Test Example 2

Male Wistar rats (8 weeks old) were anesthetized with pentobarbital (40 mg/kg) and cortices of their left kidneys were partly removed. After 3 to 7 days, their whole right kidneys were removed. The overall excision of kidneys were 1 plus three fourth to 1 plus for fifth. As the test compound, 13,14-dihydro-15-keto-16-R,S-fluoroprostaglandin $E_2$ methyl ester was suspended in distilled water and administered orally to the surgically injured animals (3 per group) at a dose of 2 mg/kg/ml on continuous 14 days starting from the day after 14 days the operation. The dose was increased to 3 mg/kg on and after day 10 of administration because animals came not to have diarrhea about that day. The control group received the same volume of distilled water. One week after the start of medication, blood the total blood was taken from ventral aorta of each animal and serum was assayed for Na, K and Cl concentrations. After 2 hours of the last medication, feces were collected and extracted with a predetermined amount of distilled water. The extract was centrifuged and the supernatant was assayed for electrolytes. Weight and water intake of the rats were measured at almost daily.

The results are summarized in the following Tables.

TABLE 4

| | Weight (g) | | | |
|---|---|---|---|---|
| | Control group | | Test group | |
| Days of medication | mean | SD | mean | SD |
| 0 | 332.2 | 31.3 | 341.7 | 23.9 |
| 1 | 345.9 | 35.3 | 321.8 | 24.3 |
| 2 | 324.0 | 23.0 | 311.8 | 15.7 |
| 3 | 345.4 | 25.7 | 313.8 | 10.8 |
| 4 | 339.4 | 22.5 | 319.3 | 10.3 |
| 5 | 344.9 | 25.1 | 336.7 | 12.8 |
| 7 | 352.7 | 31.0 | 351.6 | 15.5 |
| 8 | 348.9 | 25.7 | 341.9 | 17.4 |
| 9 | 335.6 | 26.0 | 341.0 | 15.6 |

TABLE 4-continued

| | Weight (g) | | | |
|---|---|---|---|---|
| | Control group | | Test group | |
| Days of medication | mean | SD | mean | SD |
| 10 | 360.6 | 32.8 | 348.6 | 23.5 |
| 11 | 360.6 | 21.1 | 359.6 | 20.3 |
| 12 | 355.2 | 28.2 | 356.7 | 17.1 |
| 13 | 357.9 | 27.2 | 359.5 | 20.2 |
| 14 | 337.7 | 8.6 | 364.8 | 15.0 |

TABLE 5

| | Water intake (ml/day) | | | |
|---|---|---|---|---|
| | Control group | | Test group | |
| Days of medication | mean | SD | mean | SD |
| 1 | 77.6 | 12.4 | 44.2 | 7.1 |
| 2 | 72.1 | 10.2 | 51.4 | 4.5 |
| 3 | | | 48.3 | 13.7 |
| 4 | 69.0 | 10.2 | 66.3 | 16.3 |
| 5 | 74.6 | 9.5 | 99.8 | 18.3 |
| 8 | 70.6 | 5.1 | 99.8 | 18.3 |
| 9 | 73.4 | 7.0 | 95.9 | 16.1 |
| 10 | 75.4 | 5.0 | | |
| 11 | 71.3 | 7.1 | 88.8 | 5.2 |
| 12 | 73.8 | 3.2 | 81.5 | 9.8 |
| 13 | 72.1 | 4.3 | 89.5 | 5.9 |

TABLE 6

| | | Serum | | |
|---|---|---|---|---|
| Group | | Na | K | Cl |
| untreated | mean | 140.3 | 4.03 | 108.6 |
| | ±SD | ±5.4 | ±0.21 | ±2.9 |
| 2 weeks after | mean | 142.6 | 4.42 | 104.0 |
| operation | ±SD | ±1.7 | ±0.30 | ±1.0 |
| medicated | mean | 141.7 | 3.79 | 104.4 |
| control | ±SD | ±5.6 | ±0.69 | ±3.8 |
| 1 week | mean | 144.3 | 3.57** | 107.1 |
| medicated | ±SD | ±1.8 | ±0.66 | ±2.4 |
| medicated | mean | 142.9 | 4.04 | 104.2 |
| control | ±SD | ±4.3 | ±0.39 | ±2.9 |
| 2 weeks | mean | 147.5 | 3.32** | 108.7 |
| medicated | ±SD | ±1.7 | ±0.12 | ±1.0 |

*P < 0.05
**P < 0.1

TABLE 7

| | | Serum | |
|---|---|---|---|
| | | control | 2 mg/kg |
| | | mean ± S.D. | mean ± S.D. |
| Na | (mmol/l) | 142.9 ± 4.3 | 147.5 ± 1.7 |
| K | (mmol/l) | 4.64 ± 0.39 | 3.32 ± 0.12 |
| Cl | (mmol/l) | 104.2 ± 2.9 | 108.7 ± 1.0 |

TABLE 8

| | | Feces (2 weeks medication) | | |
|---|---|---|---|---|
| group | | Na mg | K mg | Cl mg |
| control | mean | 0.28 | 1.74 | 4.51 |
| test | mean | 14.01 | 21.46 | 40.35 |
| | ±SD | ±10.35 | ±6.35 | ±11.03 |

For the above result, it can be clearly seen that, after two weeks of renal injury, potassium ion concentration in the blood was increased in the injured group by about 10% as compared with the intact group and that, after two weeks of the onset of medication, potassium ion concentration was significantly decreased in the medicated group as compared with the control group and further, 2 hours after the medication, electolyte in feces of the medicated group were twelve times larger than in feces of the control group.

Test Example 3

The procedure of Test Example 2 was repeated except that 13,14-dihydro-15-keto-16,16-difluoro-PGE$_2$ (1.0 mg/kg) was used as the test compound. Contents of electorlyte in feces (after 5 days of medication) and in the serum (after 7 days of medication) are shown in the following Tables.

TABLE 9

| | | | Feces | | |
|---|---|---|---|---|---|
| day | | | Na mg | K mg | Cl mg |
| 5 | Control | Mean | 0.60 | 1.28 | 3.85 |
| | | S.D. | ±0.42 | ±0.52 | ±1.42 |
| | Medicated | Mean | 4.47* | 7.24** | 13.57*** |
| | | S.D. | ±2.15 | ±1.55 | ±2.55 |

TABLE 10

| | | | Serum | | |
|---|---|---|---|---|---|
| day | | | Na mmol/l | K mmol/l | Cl mmol/l |
| 5 | Control | Mean | 139.4 | 10.09 | 105.2 |
| | | S.D. | ±2.1 | ±1.60 | ±1.5 |
| | Medicated | Mean | 141.1 | 9.22 | 105.4 |
| | | S.D. | ±3.4 | ±0.60 | ±3.8 |

What we claimed is:

1. A method for inducing decrease in potassium ion concentration in the blood which comprises administering, to a subject having an increased potassium ion concentration in the blood, a derivative of a prostanoic acid having the skeleton

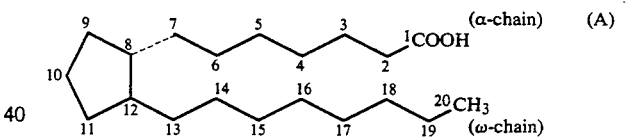

in an amount effective in inducing decrease in potassium ion concentration in the blood wherein said concentration is increased.

2. The method according to claim 1, for compensating reduced renal function.

3. The method according to claim 1, for treating renal insufficiency.

4. The method according to claim 1, wherein the prostanoic acid derivative has one or two halogen atoms at position 16.

5. The method according to claim 1, wherein the prostanoic acid derivative has an oxo group at position 15.

6. The method according to claim 1, wherein the prostanoic acid derivative has a saturated bond between positions 13 and 14.

7. The method according to claim 1, wherein the prostanoic acid is a prostaglandin derivative.

8. The method according to claim 1, wherein the prostanoic acid derivative is a 15-keto-16-mono- or di-fluoroprostaglandin compound.

9. A method for improving extracorporeal excretion of potassium ion in the blood which comprises administering, to a subject having an increased potassium ion concentration in the blood, a derivative of a prostanoic acid having the skeleton

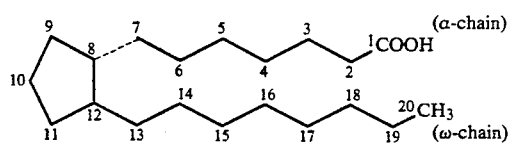

in an amount effective in improving extracorporeal excretion of potassium ion concentration is increased.

10. The method according to claim 9, wherein the excretion occurs through the intestine.

11. The method according to claim 9, for treating hyperkalemia.

12. The method according to claim 9, for compensating reduced renal function.

13. The method according to claim 9, for treating renal insufficiency.

14. The method according to claim 9, wherein the prostanoic acid derivative has one or two halogen atoms at position 16.

15. The method according to claim 9, wherein the prostanoic acid derivative has an oxo group at position 15.

16. The method according to claim 9, wherein the prostanoic acid derivative has a saturated bond between positions 13 and 14.

17. The method according to claim 9, wherein the prostanoic acid is a prostaglandin derivative.

18. The method according to claim 9, wherein the prostanoic acid derivative is a 15-keto-16-mono- or di-fluoroprostaglandin compound.

19. The method according to claim 7 wherein the derivative of a prostanoic acid is a PGA, PGB, PGC, PGD, PGE, PGF, PGG, PGH, PGI or PGJ.

20. The method of claim 17 wherein the derivative of a prostanoic acid is a PGA, PGB, PGC, PGD, PGE, PGF, PGG, PGH, PGI or PGJ.

* * * * *